United States Patent [19]

Toner et al.

[11] Patent Number: 4,476,007

[45] Date of Patent: Oct. 9, 1984

[54] HEMISPHERANDS AND SODIUM-SELECTIVE COMPOSITIONS AND ELECTRODES CONTAINING SAME

[75] Inventors: John L. Toner, Webster; Daniel S. Daniel; Susan M. Geer, both of Rochester, all of N.Y.

[73] Assignee: Eastman Kodak Company, Rochester, N.Y.

[21] Appl. No.: 496,740

[22] Filed: May 20, 1983

[51] Int. Cl.$^3$ .................. C07D 273/01; G01N 27/30
[52] U.S. Cl. .................................. 204/417; 204/418; 546/39
[58] Field of Search ..................... 204/417, 418, 1 A; 546/39

[56] References Cited

U.S. PATENT DOCUMENTS

| | | | |
|---|---|---|---|
| 3,562,129 | 2/1971 | Simon | 204/418 |
| 3,598,868 | 8/1971 | Cram et al. | 562/429 |
| 3,657,095 | 4/1972 | Tosteson | 204/409 |
| 3,743,588 | 7/1973 | Brown et al. | 204/403 |
| 3,753,887 | 8/1973 | Kedem et al. | 204/417 |
| 3,856,649 | 12/1974 | Genshaw et al. | 204/418 |
| 3,957,607 | 5/1976 | Simon et al. | 204/180 P |
| 3,965,116 | 6/1976 | Cram | 549/348 |
| 4,001,279 | 1/1977 | Cram | 549/348 |
| 4,043,979 | 8/1977 | Cram | 525/332.2 |
| 4,080,337 | 3/1978 | Cram | 260/244.4 |
| 4,113,959 | 9/1978 | Cram | 560/38 |
| 4,128,556 | 12/1978 | Cram | 546/26 |
| 4,134,798 | 1/1979 | Pinsky | 204/1 T |
| 4,214,968 | 7/1980 | Battaglia et al. | 204/418 |
| 4,227,003 | 10/1980 | Debono et al. | 548/216 |
| 4,236,987 | 12/1980 | Schindler et al. | 204/417 |
| 4,271,002 | 6/1981 | Hawkins | 204/418 |

FOREIGN PATENT DOCUMENTS

| | | |
|---|---|---|
| 2924285 | of 0000 | Fed. Rep. of Germany. |
| 53137080 | of 0000 | Japan. |
| 54151994 | of 0000 | Japan. |
| 5624571 | of 0000 | Japan. |
| 8113502 | of 0000 | Japan. |

OTHER PUBLICATIONS

E. Pretsch et al., Research/Development Magazine, vol. 25, No. 3, pp. 20-23, Mar. 1974.
Research Proposal Submitted to the Division of Physical Research, U.S. Atomic Energy Commission, Washington, D.C. 20545.
Renewal Proposal for AEC Contract AT(04-3)34, P.A. 218-Jan. 15, 1975-pp. 1-13.
Renewal Proposal for ERDA Contract AT(04-3)34, P.A. 218-Jan. 15, 1976-pp. 1-14.
Renewal Proposal for ERDA Contract AT(04-3)34, P.A. 218-Jan. 15, 1977-pp. 1-22.
ERDA Contract Renewal Proposal for 1978-1979-pp. 2-19.
Renewal Proposal for DOE Contract AT(04-3)34, P.A. 218-pp. 2-17, (1979-1980).

Renewal Proposal for DOE Contract DOE EY 76-S-0-3-0034, P.A. 218-pp. 2-18, 25-28, (1981-1982).
Third Progress Report for ERDA Contract AT(-04-3)34, P.A. 218, pp. 1-20, Jan. 15, 1977.
Fourth Progress Report for ERDA Contract AT(-04-3)34, P.A. 218, 1-24, Jan. 15, 1978.
Fifth Progress Report for Division of Basic Energy Sciences, Dept. of Energy, Contract AT(04-3)34, P.A. 218, pp. 1-25, Jan. 15, 1979.

(List continued on next page.)

*Primary Examiner*—G. L. Kaplan
*Attorney, Agent, or Firm*—J. Lanny Tucker

[57] ABSTRACT

Ion-selective compositions which comprise an ion carrier, a compound capable of solvating the ion carrier, and a supporting matrix are disclosed.

The ion carriers of this invention are hemispherand compounds represented by the formula

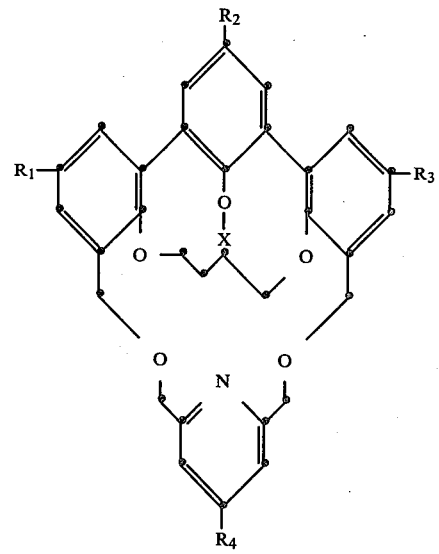

wherein $R_1$, $R_2$, $R_3$ and $R_4$ are independently hydrogen, alkyl, alkenyl, cycloalkyl, aryl or a heterocyclic group; and X is benzyl or an electron donating group capable of forming at least one coordinating site for sodium ions. A preferred hemispherand according to this invention is 2'-benzyloxy-3,3''-[2,6-pyridylenebis(methyleneoxymethylene)]-2,2''-tetramethylenedioxy-5,5',5''-trimethyl-1,1':3',1''-terphenyl. These compounds and the compositions containing same are particularly useful in ion-selective electrodes. Such an electrode is capable of selectively transporting sodium ions in preference to other cations. Dry-operative electrodes using these ion-selective compositions as membranes are also disclosed.

25 Claims, No Drawings

OTHER PUBLICATIONS

"III. Research Results Obtained for the Reporting Period, May 1, 1979 through Apr. 30, 1980", pp. 5-19. Seventh Progress Report for Division of Basic Energy Sciences, Dept. of Energy, Contract DOE EY 76-S-0-3-0034, P.A. 218, pp. 1-13, Jan. 15, 1981.

"Concept, Structure, and Binding in Complexation", *Topics in Current Chemistry*, 98, pp. 43-106, 1981.

Journal of the American Chemical Society, 101, pp. 3545-3566, Jun. 1979.

Journal of the Chemical Society, Chemical Communications, pp. 948-950, 1979.

J.A.C.S., 101, pp. 6752-6754, Oct. 1979; 98, pp. 4018-4020, Jun., 1976; 103, pp. 5594-5596, 1981; 103, pp. 6228-6232, 1981; 101, pp. 4928-4941, Aug., 1979; 99, pp. 3880-3882, May, 1977; 103, pp. 3929-3931, 1981.

J. Org. Chem., 44, No. 14, 1979, pp. 2538-2550.

J. Chem. Soc. Chem. Comm., pp. 958-959, (1976).

J. Org. Chem., 44, pp. 2226-2233, 1979.

Cram, D. J., *Science*, "Cavitands: Organic Hosts with Enforced Cavities", Mar. 11, 1983, vol. 219, No. 4589, pp. 1177-1183.

HEMISPHERANDS AND SODIUM-SELECTIVE COMPOSITIONS AND ELECTRODES CONTAINING SAME

RELATED APPLICATIONS

U.S. Ser. No. 496,739, filed on even date herewith entitled HEMISPHERANDS IN ION-SELECTIVE COMPOSITIONS, which is a continuation-in-part of U.S. Ser. No. 332,904, filed Dec. 21, 1981. This application is also cross referenced in U.S. Ser. No. 496,738 filed on even date herewith entitled SODIUM-SELECTIVE COMPOSITIONS AND ELECTRODES CONTAINING SAME.

FIELD OF THE INVENTION

This invention relates to particular hemispherand compounds and to compositions containing same which are useful as ion-selective membranes. In one particularly preferred embodiment, the compositions are used as ion-selective membranes which are capable of selectively transporting sodium ions in preference to other cations in ion-selective electrodes of various types.

DESCRIPTION RELATIVE TO THE PRIOR ART

In the diagnosis and treatment of various diseases as well as in preventative health checkups, it is becoming increasingly important to monitor the concentrations of certain ions (e.g. cations) in a patient's body. Cations which have merited considerable attention in the diagnosis and treatment of heart disease, manic depressive psychosis, kidney disease, diabetes and hypertension are alkali metal ions, e.g. lithium, sodium and potassium.

One type of ion-selective electrode has an electrode body (usually a glass container) containing a reference solution in contact with a half-cell of known potential (a reference electrode) and an ion-selective glass membrane located in an aperture in the electrode body. The ion-selective membrane is mounted in such a fashion that, when the electrode is immersed in the unknown solution, the membrane contacts both the reference and unknown solutions. A metal probe coated with a layer of insoluble salt of the metal in the reference solution and immersed therein serves as one of the contacts for measuring the potential between the electrodes and provides a reference potential for the electrode. The sensitivity of the electrode to an ion in solution is determined by the composition of the glass membrane. This type of electrode is referred to in the art as a "barrel" electrode.

In addition to the glass membranes, polymeric ion-sensitive membranes are also known. These membranes generally comprise a polymeric binder or support as the supporting matrix which is impregnated with a solution of an ion-sensitive carrier in a carrier solvent. The ion-sensitive carrier is a compound which is capable of sequentially complexing the desired ion, transporting the ion through the composition and releasing the ion. This compound is also referred to in the art as an "ionophore" or "ion carrier". Depending upon the ionophore, solvent and binder, membranes of this type can be used to detect a particular ion preferentially to other ions which may be in the solution.

A significant advance in the ion-selective-electrode art is the dry-operative electrode described in U.S. Pat. No. 4,214,968 (issued July 29, 1980 to Battaglia et al). Prior to the discovery of such dry-operative ion-selective electrodes, electrodes had to be either stored in an aqueous solution or treated with aqueous solution just prior to use in an ion-activity-determining operation. The term "dry-operative" refers to an ion-selective electrode which provides reproducible potentiometric determination of ion activity which is related to the ion concentration of an aqueous test solution with no requirement for wet storage or preconditioning prior to use.

One of the specific ion-selective electrodes disclosed in the examples of Battagalia et al is a sodium ion-selective electrode using methyl monensin as the sodium-selective ionophore. While methyl monensin is a useful ion-selective membrane for a variety of purposes, still further improvements, particularly in the selectivity of the electrode for sodium over potassium, are desired.

Copending U.S. Ser. No. 496,739 filed on even date herewith, which is a continuation-in-part of U.S. Ser. No. 332,904, filed Dec. 21, 1981, describes a generic class of hemispherands useful as ionophores in ion-selective compositions, membranes and electrodes. Specifically useful hemispherands are represented by the structural formula:

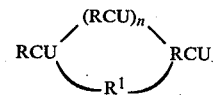

wherein n is an integer of from 1 to 3; each RCU is a rigid cyclic unit individually selected from the group consisting of units of the structure:

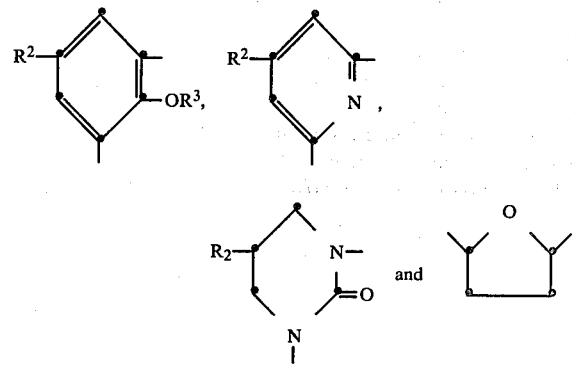

wherein:

$R^2$ is hydrogen or a group selected from alkyl, alkenyl, cycloalkyl, aryl and alkyl, alkenyl, cycloalkyl and aryl groups containing heteroatoms or containing heteroatom substituents;

$R^3$ is an alkyl or alkenyl group or, when taken together with an $R^3$ group from another RCU, forms an alkylene group or an alkylene group interrupted with heteroatoms; and $R^1$ represents the atoms necessary to complete a macrocyclic ring structure, with the proviso that $R^1$ contains (a) at least one coordinating site for ions and (b) at least two alkylene groups as part of the ring structure.

The hemispherands described in our copending application have been found useful as ionophores in ion-selective compositions, membranes and electrodes used for assaying for ions in general in various biological fluids, e.g. blood serum. They generally provide improved selectivity of one ion over another compared to previously known ionophores, e.g. methyl monensin.

However, a higher degree of selectivity of sodium over potassium is needed for the uncorrected determination of sodium in urine and some other biological fluids (e.g. intracellular fluids containing red blood cells) because urine and those fluids either contain widely fluctuating concentrations of potassium and sodium ions, or generally have more potassium ions than sodium ions. Generally, it is important in analyzing urine and such fluids that the ratio of $k_{Na+}$ to $k_{K+}$ to be greater than about 100. Such a ratio indicates high sodium selectivity. These k values are selectivity coefficients and are defined in more detail in Example 2 hereinbelow. The hemispherands described in our copending application, as a class, do not provide the high selectivity for sodium ion required for such uncorrected analyses. Hence, there is a continuing search for ionophores and ion-selective compositions containing same which are highly selective for sodium ions in solution.

SUMMARY OF THE INVENTION

It has been found that certain lipophilic hemispherands are useful as ionophores in ion-selective compositions which exhibit unexpectedly high selectivity for sodium ions over other cations in solution and particularly over potassium ions. These hemispherands have been found to be very useful as ionophores in sodium-selective compositions (e.g. membranes) and electrodes used to assay for sodium ions in urine or other fluid samples (either human or animal). The sodium selectivity of the hemispherands of this invention is established by the fact that the ratio of $k_{Na+}$ to $k_{K+}$ is greater than about 100. The high selectivity of these hemispherands is particularly surprising because extremely closely related compounds specifically described in our co-pending continuation-in-part application mentioned hereinabove, do not function as effectively as sodium-selective ionophores as do the hemispherands of this invention (see Example 2 hereinbelow).

Therefore, the present invention provides the novel hemispherands having the structure:

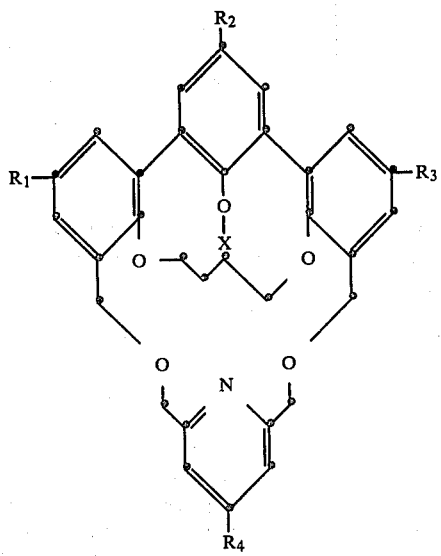

wherein $R_1$, $R_2$, $R_3$ and $R_4$ are independently hydrogen, alkyl, alkenyl, cycloalkyl, aryl or a heterocyclic group; and X is benzyl or an electron donating group capable of forming at least one coordinating site for sodium ions.

In addition, this invention provides a composition comprising such a hemispherand, a compound capable of solvating it and a supporting matrix. This composition is useful as an ion-selective membrane.

In preferred embodiments, the solvating compound is a hydrophobic carrier solvent and the supporting matrix is a hydrophobic binder.

The compositions described above are also useful in ion-selective electrodes. Thus, in another aspect of the present invention, there is provided an ion-selective electrode having an ion-selective membrane composition comprising an ionophore which is the lipophilic hemispherand described hereinabove, a compound capable of solvating the hemispherand compound, and a supporting matrix.

The compositions herein are also useful in dry-operative ion-selective electrodes. Thus, in still another aspect of the present invention there is provided a dry-operative ion-selective electrode comprising the lipophilic hemispherand ionophore described hereinabove dissolved in a compound capable of solvating the hemispherand compound.

DETAILED DESCRIPTION OF THE INVENTION

Generically, hemispherands and related compounds are compounds which were first developed by Dr. D. J. Cram and his coworkers (see *Journal of the American Chemical Society*, 101:22, October, 1979, and 101:13, June, 1979; *J. C. S. Chem. Comm.*, page 948, 1979).

A hemispherand is a macrocyclic compound wherein at least a portion of the macrocyclic ring contains contiguous rigid cyclic units, at least some of these units having coordinating sites for ions. The rigid cyclic units are sufficient in number to rigidize a portion of the macrocyclic ring structure. The coordinating sites in the cyclic units are oriented so as to face the interior of the macrocycle, thereby forming the rigidized portion of the macrocyclic cavity in the molecule for receiving ions.

Lipophilic hemispherands are hemispherands which contain no solubilizing groups such as carboxylic acid groups or sulfonic acid groups, or which contain sufficiently large oil-soluble groups to render the molecule oil-soluble, e.g., capable of forming a 4%-by-weight solution of the hemispherand in a hydrophobic organic solvent.

The hemispherands of this invention can be represented by the structure:

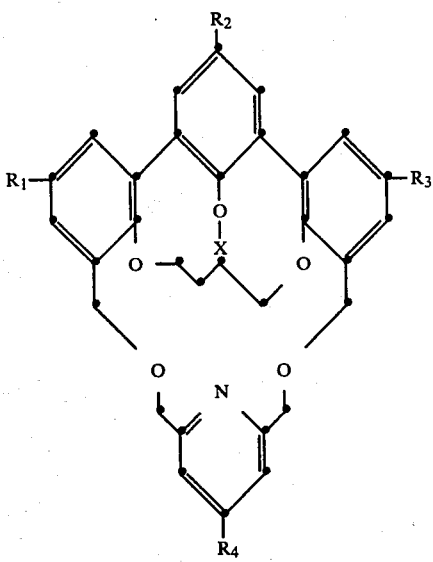

wherein $R_1$, $R_2$, $R_3$ and $R_4$ are independently hydrogen; or a group selected from alkyl (substituted or unsubstituted), preferably of from 1 to 12 carbon atoms (e.g. methyl, ethyl, isopropyl, t-butyl, hexyl, etc.), alkenyl (substituted or unsubstituted), preferably of from 2 to 12 carbon atoms (e.g. allyl, vinyl, 1-propenyl, etc.) cycloalkyl (substituted or unsubstituted), preferably of from 3 to 10 carbon atoms (e.g. cyclopropyl, cyclohexyl, etc.), aryl (substituted or unsubstituted), preferably of from 6 to 12 carbon atoms (e.g. phenyl, tolyl, xylyl, methoxyphenyl, etc.), and heterocyclic groups (substituted or unsubstituted), preferably of 5 to 10 nuclear atoms (e.g. pyridyl, etc.). Any of these R groups can be substituted with one or more halo, nitro, amino, alkoxy or other suitable groups as known by one skilled in the art. Preferably, each of $R_1$, $R_2$, $R_3$ and $R_4$ is hydrogen or alkyl (e.g. of 1 to 6 carbon atoms). More preferably, two or more of $R_1$, $R_2$, $R_3$ and $R_4$ are the same alkyl, e.g. methyl.

X can be benzyl (unsubstituted or substituted with alkoxy, amino, nitro, alkyl or halo). Alternatively, X can be an electron donating group capable of forming at least one (and preferably, only one) coordinating site. Such groups include pyridylalkylene (substituted or unsubstituted) e.g. pyridylmethylene and alkyl groups, preferably of 1 to 6 carbon atoms having carbonyl, thiono, amino (substituted or unsubstituted), alkoxy, thio, sulfinyl, phosphinyl, phosphinyl oxide, tetrahydrofuryl or furyl substituents. Preferably, X is unsubstituted benzyl (i.e. $-CH_2C_6H_5$).

The hemispherand can also have one or more substituents in place of any hydrogen atoms which can be removed, e.g. in the methylene groups or on the aromatic rings.

A preferred hemispherand is 2'-benzyloxy-3,3''-[2,6-pyridylenebis(methyleneoxymethylene)]-2,2'''-tetramethylenedioxy-5,5',5'''-trimethyl-1,1':3',1''-terphenyl. This hemispherand is prepared by the procedure described in Example 1 hereinbelow. Other hemispherands within the scope of this invention are similarly prepared. Another preferred hemispherand is 2'-p-methoxybenzyloxy-3,3''-[2,6-pyridylenebis(methyleneoxymethylene)]-2,2'''-tetramethylenedioxy-5,5'',5'''-trimethyl-1,1':3',1''-terphenyl.

In addition to the lipophilic hemispherand, the compositions of the present invention include a compound which is capable of solvating the hemispherand. Solvation is necessary so that sodium ions are transported through the membrane by the solvated hemispherand. In some embodiments, one or more polymeric binders which are capable of solvating the hemispherand are used. If the polymer is capable of dissolving, at least partially, the hemispherand, it is useful in this embodiment. Exemplary polymers which are so useful are described in U.S. Pat. No. 3,419,634 (issued Dec. 31, 1968 to Vaughn, Jr.). The preparation of ion-selective membranes using these solvating polymers is described in U.S. Pat. No. 3,743,588 (issued July 3, 1973 to Brown, Jr. et al). In these embodiments, the polymer functions as both the compound which is capable of solvating the hemispherand and the supporting matrix for the composition.

In other and preferred embodiments, the hemispherand is solvated by one or more separate organic solvents and the supporting matrix is a separate component. Such a matrix must allow for the transport of the sodium ions which are bound to the hemispherand in the organic solvent. For example, a porous glass support is useful as the supporting matrix. In these embodiments, the hemispherand is dissolved in the organic solvent and then the resulting solution is imbibed into the porous glass support to provide an ion-selective membrane. In other embodiments, the solution of the hemispherand is dispersed in a hydrophobic binder. By "hydrophobic" is meant substantially water-insoluble. The binder dispersion is coated and dried to produce an ion-selective membrane according to the present invention.

Where a separate solvent is used to solvate the hemispherand, the solvent can be any of a wide variety of solvents, provided that it is capable of at least partially dissolving the hemispherand. The solvent, sometimes referred to in the art as a carrier solvent, provides sodium ion mobility in the membrane. If a hydrophobic binder is used as the supporting matrix, the solvent must be compatible with the binder. Useful carrier solvents are hydrophobic organic solvents including phthalates, sebacates, aromatic and aliphatic ethers, phosphates, mixed aromatic aliphatic phosphonates, adipates, nitrated ethers or esters and mixtures of these solvents. Particularly useful solvents include dibutyl sebacate, bromophenyl phenyl ether, bis(2-ethylhexyl) sebacate, bis(2-ethylhexyl) 4-nitrophthalate, o-nitrophenyl valerate, dioctyl phenylphosphonate, o-nitrophenyl phenyl ether, o-nitrophenyl octyl ether, triisodecyl trimellitate, dimethyl phthalate, diisodecyl phthalate and tris(2-ethylhexyl) phosphate. Diisodecyl phthalate is a particularly preferred solvent when 2'-benzyloxy-3,3''-[2,6-pyridylenebis(methylenoxymethyolene)]2,2''-tetramethylenedioxy-5,5',5''-trimethyl-1,1':3',1''-terphenyl is used as the ionophore in the sodium-selective compositions and electrodes of this invention.

If the hemispherand is included in a carrier solvent as described above, a membrane is formed using a dispersion of the solvent-hemispherand in one or more binders as the supporting matrix. Useful binders include hydrophobic natural or synthetic polymers capable of forming thin films of sufficient permeability to produce, in combination with the hemispherands and carrier solvent, ionic mobility across the membrane. Useful polymers include poly(vinyl chloride); poly(vinylidene chloride); poly(acrylonitrile); polyurethanes, particularly aromatic polyurethanes; copolymers of vinyl chloride and vinylidene chloride; poly(vinyl butyral); poly(vinyl formal); poly(vinyl acetate); silicone elastomers; and copolymers of vinyl alcohol, cellulose esters and polycarbonates. Other useful polymers include carboxylated polymers of poly(vinyl chloride) and mixtures and copolymers of these materials. Membranes including binders, the hemispherands and carrier solvents are prepared using conventional film-coating or casting techniques.

The membranes of the present invention contain the described components over a wide range of concentrations or coverages. The coverage of the hemispherand depends upon the compound used to solvate it, as well as other factors. The preferred membranes comprise a hydrophobic binder having the solvent and hemispherand dispersed therein. In these membranes, hemispherand coverages of between about 0.1 $g/m^2$ and 2.0 $g/m^2$ are useful and coverages between 0.2 $g/m^2$ and 0.8 $g/m^2$ are preferred.

The carrier solvent is present in an amount sufficient to solvate the hemispherand. The amount therefore depends on the particular solvent and hemispherand chosen. Generally, more solvent is used than is necessary to solvate the hemispherand so that it remains solvated under a variety of storage conditions. A 100 percent or 500 percent excess on a weight basis is useful. Usually, the coverage of carrier solvent will be within the range of about 2 $g/m^2$ to 24 $g/m^2$.

The amount of hydrophobic binder which is present is determined by the desired thickness of the membrane and by the necessity for providing support for the hemispherand-solvent dispersion. The membranes generally have a thickness in the range of from about 2 $\mu$m to about 20 $\mu$m. The binder coverage is usually between about 2 and 24, and preferably from about 3 to about 12 $g/m^2$.

In addition to the binder, hemispherand and solvent, the membranes of the present invention optionally contain other components such as surfactants and plasticizers in amounts known to those skilled in the art.

As noted, surfactants are useful components of the described membranes. The surfactants serve a variety of functions including improving the coatability of the membrane composition and improving the solvation of the hemispherand by the binder or solvent. Useful surfactants include nonionic surfactants such as the alkylaryl polyether alcohols (Tritons TM) available from Rohm and Haas Co; (p-isononylphenoxy)polyglycidol (Surfactant 10G TM) available from Olin Mathieson Corp; polyoxyethylene (20) oleyl ether (Brij 98 TM), polyoxyethylene sorbitan monolaurate (Tween 20 TM) and Span 80 TM, all available from Atlas Chemical Industries; poly(dimethyl-comethylphenyl siloxane) (DC-510 TM) available from Dow Corning; Zonyl FSN TM available from E. I. duPont; and fluorochemical surfactant FC134 TM available from 3M Co.

A useful ion-selective electrode comprises:
(a) a reference electrode in contact with
(b) a reference composition which is, in turn, in contact with one side of
(c) an ion-selective membrane of the type described hereinabove.

In one embodiment, the ion-selective electrode is in the form of a glass tube. The ion-selective membrane forms the bottom of the tube. The tube is at least partially filled with a salt solution of known concentration forming the reference composition. Immersed in the reference composition is a reference electrode which is a metal electrode having a thin metal salt layer on its outer surface. The ion-selective electrode is used by immersing at least the membrane of the electrode in the unknown solution. One side of a voltmeter is connected to the reference electrode immersed in the reference composition and the other side is connected to a conducting probe in the unknown solution. The potential which develops across the voltmeter is proportional to the difference in ion concentration between the unknown solution and the reference composition.

The membranes of the present invention are useful in a variety of electrode structures. For example, the membranes of the present invention are useful in place of, or in addition to, the glass ion-selective membrane of a conventional barrel-type electrode. Useful electrodes of this type are disclosed, for example, in U.S. Pat. Nos. 3,598,713, 3,502,560, 3,562,129, 3,691,047, 3,753,887, 3,833,495, 3,671,414 and 3,743,588. The membranes are also useful in the ion-selective electrodes described in Japanese Patent Publications Nos. 17851/1982 and 17852/1982, both published Jan. 29, 1982, and particularly in the dry ion-selective electrodes described therein.

In particularly preferred embodiments, the hemispherand-containing membrane of the present invention is used in a dry-operative ion-selective electrode as described in U.S. Pat. No. 4,214,968 noted hereinbove. In this embodiment, there is provided a dry-operative ion-selective electrode comprising:
(a) a dried internal reference element comprising the dried residue of a solution of a salt and a hydrophilic polymeric binder in a solvent for the polymer and the salt and,
(b) in contact with the reference element, a hydrophobic ion-selective membrane of predetermined uniform thickness in regions thereof intended for contact with the sample for analysis, the membrane comprising a hydrophobic binder having distributed therein the lipophilic hemispherand ion carrier described hereinabove dissolved in a carrier solvent.

In this embodiment of the present invention, the electrodes are made by a process using components which are described in U.S. Pat. No. 4,214,968 (noted hereinabove), the disclosure of which is hereby incorporated by reference in its entirety. As used throughout this specification and in the claims, the expressions "dry-operative", "dried" and "uniform" have the meanings defined in the U.S. Pat. No. 4,214,968.

The membranes and electrodes of this invention can be used to determine the concentration of sodium in an aqueous solution, e.g. biological fluids such as blood sera and urine. It is particularly useful in determining sodium ion concentration in urine having a high potassium ion concentration. Generally, a portion of the solution to be assayed is brought into contact with the electrode (e.g a dry ion-selective electrode) described hereinabove which is capable of making potentiometric measurements related to the sodium ion concentration. Subsequently, the difference in potential between the portion of aqueous solution and the reference electrode is measured. Preferably, a drop of the aqueous solution is spotted onto the ion-sensitive membrane of such electrode, but other ways of contacting the electrode with the solution are acceptable.

The following examples are presented to illustrate the practice of this invention.

EXAMPLE 1

Preparation of 2'-benzyloxy-3,3"[2,6-pyridylenebis(methyleneoxymethylene)]-2,2"'-tetramethylenedioxy-5,5',5"-trimethyl-1,1':3',1"-terphenyl This hemispherand was prepared using a procedure which is a modification of that described by Cram et al in the *Journal of the Americal Chemical Society*, 101, pp. 3553–66 (1979). A solution of $FeCl_3$ (1 Kg, 6 mol) in 3 L of water was added to a solution of p-cresol (115 g, 1.1 mol) in 19 L of water. The resulting solution was allowed to stand for 3 weeks at room temperature, after which crude 2,2',2"-trihydroxy-5,5',5"-trimethyl-1,1'-3',1"-terphenyl was isolated by filtration, drying and trituration with cyclohexane followed by recrystallization from $CH_2Cl_2$.

This terphenyl compound (30 g, 93.6 mmol) was then treated with benzyl bromide (11.15 mL, 93.7 mmol) and 1 equivalent of potassium carbonate in acetone to produce 2'-benzyloxy-2,2"-dihydroxy-5,5',5"-trimethyl-1,1':3',1"-terphenyl (28.6 g, 74% yield). This compound was subsequently allowed to react with paraformaldehyde (40.8 g, 1.36 mol) in a 1:30:4.5 ratio mixture of potassium hydroxide, isopropanol and water for about 10 days at room temperature. The resulting product, 2'-benzyloxy-2,2"-dihydroxy-3,3"-bis(hydroxymethyl)-5,5',5"-trimethyl-1,1':3',1"-terphenyl (6.8 g, 14.5 mmol) was treated with 1.2 equivalents of 1,4-dibromobutane in a 1:2:500 ratio mixture of sodium hydroxide, potassium iodide and dimethylformamide to produce 2'-benzyloxy-3,3"-bis(hydroxymethyl)-2,2"-tetramethylenedioxy-5,5',5"-trimethyl-1,1':3',1"-terphenyl (4.15 g, 55% yield).

This compound (1 g, 1.91 mmol) was brominated with tribromophosphine (0.4 ml) in 75 ml of benzene to yield the corresponding dibromide compound (1.06 g, 86% yield).

A mixture of the dibromide (1.1 mmol) and 2,6-bis(hydroxymethyl)pyridine (1.1 mmol) was added over a 72 hour period to a refluxing solution of sodium hydride in dry tetrahydrofuran. Refluxing was continued an additional 48 hours after this addition, and the reaction solution was then cooled to room temperature and carefully quenched with water. The resulting solution was extracted with methylene dichloride, the organic phase dried over $Na_2SO_4/MgSO_4$ and concentrated to produce a crude form of the desired hemispherand. The crude product was purified by chromatography on a Harris Research Corp. Chromatotron ™ with 50% $EtOAc/CH_2Cl_2$ on $SiO_2$ to provide a white powder (0.22 g, 32% yield) which was the desired hemispherand.

All intermediates and the final product exhibited mass infrared and NMR spectra consistent with the assigned structure note hereinabove. The purified hemispherand had a melting point of 234°–236° C. Analysis Calculated for $C_{41}H_{41}NO_5$: C, 78.4; H, 6.6; N, 2.2 theoretical; C, 78.3; H, 6.8; N, 2.2 actual.

EXAMPLE 2

Ion-Selective Electrode Using Hemispherand of This Invention As Ionophore

This is a comparative example illustrating the improved sodium ion selectivity of the hemispherand of this invention compared to a similar hemispherand described in our copending continuation-in-part application noted hereinabove but which is outside the scope of this invention.

The electrodes used in this example were of the format and prepared by the methods described by U.S. Pat. No. 4,214,968 referenced hereinabove. Each electrode comprised a polyester support having layers in sequence as follows: silver/silver chloride reference electrode; electrolyte layer comprising gelatin (3–6 g/m²), NaCl (1.5–3.5 g/m²), glycerol (0.25–0.4 g/m²) and Olin Surfactant 10G ™ (0.3–0.9 g/m²); and the membrane layer.

The membrane layer contained: 1.8% carboxylated poly(vinyl chloride) binder (3.0–6.0 g/m²), a carrier solvent as indicated (4–8 g/m²), the hemispherand as indicated, and the surfactant DC-510 ™ (0.03–0.09 g/m²).

Each hemispherand and a carrier solvent were incorporated in the membrane layer of an electrode as described above at coverages of about 0.1–0.6 g/m² and 6 g/m², respectively. The electrodes were tested by spotting 10 μL aliquots of solutions containing 0.05, 0.10, 0.15 or 0.30M sodium chloride and 0.10M KCl, LiCl, $NH_4Cl$, $CaCl_2$ or $MgCl_2$ onto samples of the electrode. Potentials were measured against a silver/silver chloride electrode. The potential developed for each aliquot was plotted against the concentration of sodium in the aliquot. The result was a Nernstian slope in the range of $10^{-4}$ to $10^{-1}$M sodium for each experiment.

For each experiment, the selectivity coefficients (k) for each of the cations other than sodium were calculated (sodium being defined as one) using the potential data from the appropriate aliquot. The results are shown in Table 1. In the table, BEHS is bis(2-ethylhexyl) sebacate and DIDP is diisodecyl phthalate.

TABLE I

| Hemispherand | Solvent | Selectivity Coefficients (k) | | | | | |
|---|---|---|---|---|---|---|---|
| | | $Na^+$ | $K^+$ | $Li^+$ | $NH_4^+$ | $Ca^{++}$ | $Mg^{++}$ |
| Example 1 | BEHS | 1 | 0.009 | 0.004 | 0.003 | 0.006 | 0.00078 |
| Example 1 | DIDP | 1 | 0.0057 | 0.0018 | 0.0033 | 0.007 | 0.0007 |
| HS-18* | BEHS | 1 | 0.018 | 0.008 | 0.01 | 0.01 | 0.0025 |

*HS-18 is 2'-allyloxy-3,3"-[2,6-pyridylene-bis(methyleneoxymethylene)]-2,2"-tetramethylenedioxy-5,5',5"-trimethyl-1,1':3',1"-terphenyl described in our copending continuation-in-part application noted hereinabove.

These data indicate that the hemispherands of this invention exhibit significantly improved selectivity for sodium compared to the sodium selectivity exhibited by HS-18, a similar hemispherand described in our copending C.I.P. application noted hereinabove. The selectivity of these hemispherands for sodium is established by the fact that each of the other ions tested exhibited a selectivity coefficient less than 1. The significantly improved sodium selectivity of the hemispherands and elements of this invention is established by the fact that the ratio of $k_{Na+}$ to $k_{K+}$ of those compounds and elements is greater than about 100.

The invention has been described in detail with particular reference to preferred embodiments thereof, but it will be understood that variations and modifications can be effected within the spirit and scope of the invention.

We claim:

1. A lipophilic hemispherand compound represented by the structure:

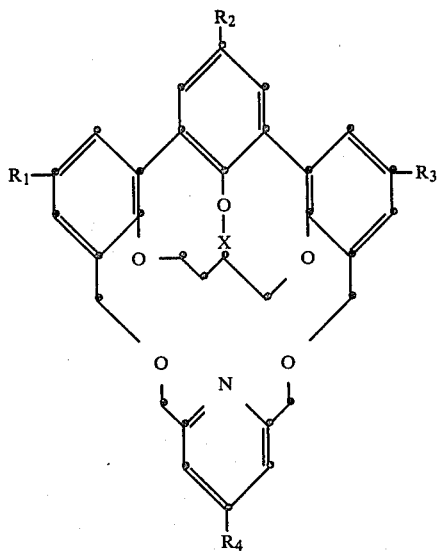

wherein $R_1$, $R_2$, $R_3$ and $R_4$ are independently hydrogen, alkyl, alkenyl, cycloalkyl, aryl or a heterocyclic group; and X is benzyl or an electron donating group capable of forming at least one coordinating site for sodium ions.

2. The compound of claim 1 wherein each of $R_1$, $R_2$, $R_3$ and $R_4$ is hydrogen or alkyl.

3. The compound of claim 1 wherein X is benzyl, pyridylalkylene, or alkyl of 1 to 6 carbon atoms substituted with a carbonyl, thiono, amino, alkoxy, thio, sulfinyl, phosphinyl, phosphinyl oxide, tetrahydrofuryl or furyl group.

4. The hemispherand of claim 3, wherein said benzyl is unsubstituted.

5. The hemispherand 2'-benzyloxy-3,3''-[2,6-pyridylenebis(methyleneoxymethylene)]-2,2''-tetramethylenedioxy-5,5',5''-trimethyl-1,1'-3',1''-terphenyl.

6. A sodium ion-selective composition comprising a lipophilic hemispherand compound represented by the structure:

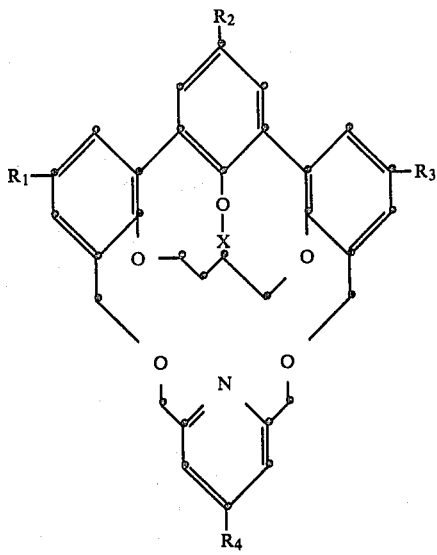

wherein $R_1$, $R_2$, $R_3$ and $R_4$ are independently hydrogen, alkyl, alkenyl, cycloalkyl, aryl or a heterocyclic group; and X is benzyl or an electron donating group capable of forming at least one coordinating site for sodium ions; and a compound capable of solvating said hemispherand.

7. The composition of claim 6 comprising a supporting matrix.

8. The composition of claim 6 wherein said solvating compound is a hydrophobic carrier solvent.

9. The composition of claim 8, wherein said carrier solvent is selected from the group consisting of phthalates, sebacates, aromatic and aliphatic ethers, phosphates, mixed aromatic-aliphatic phosphonates, adipates, nitrated ethers or esters, and mixtures thereof.

10. A composition comprising 2'-benzyloxy-3,3''-[2,6-pyridylenebis(methyleneoxymethylene)]-2,2''-tetramethylenedioxy-5,5',5''-trimethyl-1,1':3',1''-terphenyl and diisodecyl phthalate.

11. The composition of claim 10 comprising carboxylated poly(vinyl chloride).

12. A sodium ion-selective electrode having an ion selective membrane composition comprising an ionophore which is a lipophilic hemispherand compound represented by the structure:

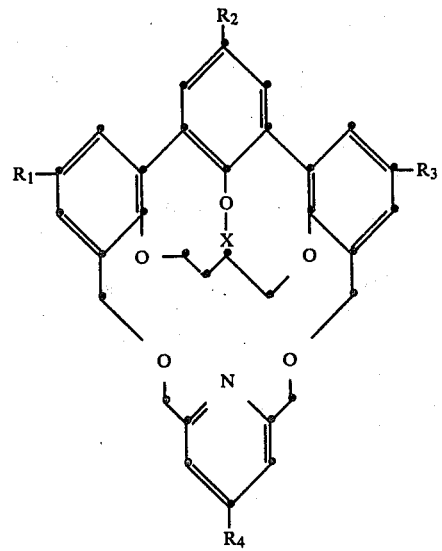

wherein $R_1$, $R_2$, $R_3$ and $R_4$ are independently hydrogen, alkyl, alkenyl, cycloalkyl, aryl or a heterocyclic group; and X is benzyl or an electron donating group capable of forming at least one coordinating site for sodium ions, a compound capable of solvating said hemispherand and a supporting matrix.

13. A sodium ion-selective electrode comprising:
(a) a reference electrode in contact with
(b) a reference composition which is, in turn, in contact with one side of
(c) an ion-selective membrane composition comprising a lipophilic hemispherand represented by the structure:

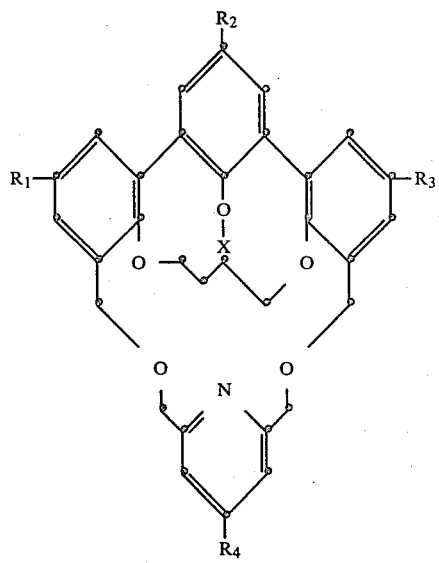

wherein $R_1$, $R_2$, $R_3$ and $R_4$ are independently hydrogen, alkyl, alkenyl, cycloalkyl, aryl or a heterocyclic group; and X is benzyl or an electron donating group capable of forming at least one coordinating site for sodium ions, a compound capable of solvating said hemispherand and a supporting matrix.

14. The electrode of claim 13, wherein said solvating compound is selected from the group consisting of phthalates, sebacates, aromatic and aliphatic ethers, phosphates, mixed aromatic-aliphatic phosphonates, adipates, nitrated ethers or esters, and mixtures thereof.

15. The electrode of claim 13, wherein said supporting matrix is porous glass.

16. The electrode of claim 13, wherein said supporting matrix is a hydrophobic polymer.

17. The electrode of claim 13, comprising a surfactant.

18. The dry-operative sodium ion-selective electrode comprising a lipopholic hemispherand ionophore dissolved in a compound capable of solvating said hemispherand compound, said hemispherand compound represented by the structure:

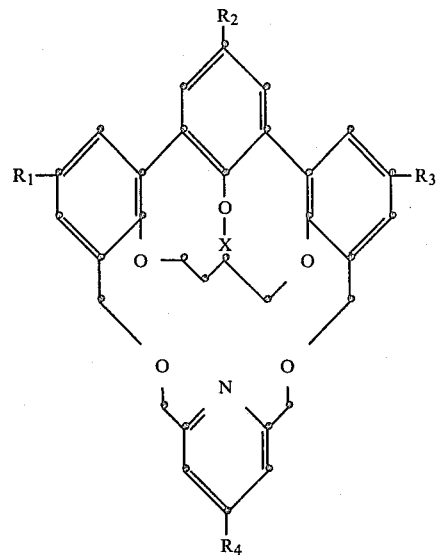

wherein $R_1$, $R_2$, $R_3$ and $R_4$ are independently hydrogen, alkyl, alkenyl, cycloalkyl, aryl or a heterocyclic group; and X is benzyl or an electron donating group capable of forming at least one coordinating site for sodium ion.

19. The electrode of claim 18 wherein said ionophore and solvating compound are distributed within a hydrophobic binder.

20. A dry-operative sodium ion-selective electrode comprising:
   (a) a dried internal reference element comprising the dried residue of a solution of a salt and a hydrophilic polymeric binder in a solvent for the polymer and the salt and,
   (b) in contact with said reference element, a hydrophobic ion-selective membrane of predetermined uniform thickness in regions thereof intended for contact with a sample for analysis, the membrane comprising a hydrophobic polymeric binder having distributed therein a hemispherand compound represented by the structure:

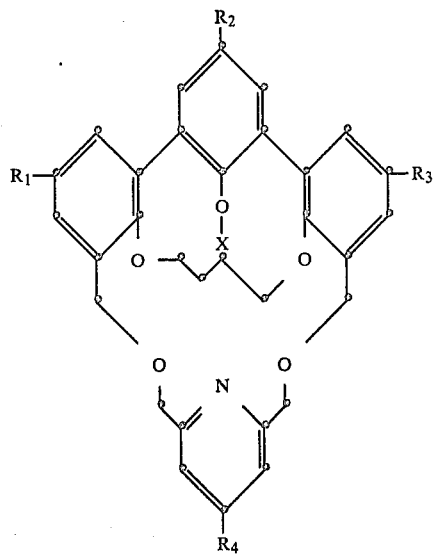

wherein $R_1$, $R_2$, $R_3$ and $R_4$ are independently hydrogen, alkyl, alkenyl, cycloalkyl, aryl or a heterocyclic group; and X is benzyl or an electron donating group capable of forming at least one coordinating site for sodium ions, dissolved in a compound capable of solvating said hemispherand, which solvating compound is a hydrophobic carrier solvent.

21. The electrode of claim 20 wherein each of $R_1$, $R_2$, $R_3$ and $R_4$ is hydrogen or alkyl.

22. The electrode of claim 20 wherein X is benzyl, pyridylalkylene, or alkyl of 1 to 6 carbon atoms substituted with a carbonyl, thiono, amino, alkoxy, thio, sulfinyl, phosphinyl, phosphinyl oxide, tetrahydrofuryl or furyl group.

23. The electrode of claim 22 wherein X is unsubstituted benzyl.

24. The electrode of claim 20, wherein said carrier solvent is selected from the group consisting of phthalates, sebacates, aromatic and aliphatic ethers, phosphates, mixed aromatic-aliphatic phosphonates, adipates, nitrated ethers and esters, and mixtures thereof.

25. A dry operative sodium ion-selective electrode comprising:
 (a) a dried internal reference element comprising the dried residue of a solution of a salt and a hydrophilic polymeric binder in a solvent for the polymer and the salt and,
 (b) in contact with said reference element, a hydrophobic ion-selective membrane of predetermined uniform thickness in regions thereof intended for contact with a sample for analysis, the membrane comprising a supporting matrix having distributed therein 2'-benzyloxy-3,3"-[2,6-pyridylenebis(methyleneoxymethylene)]-2,2"-tetramethylenedioxy-5,5',5"-trimethyl-1,1':3',1"-terphenyl, dissolved in diisodecyl phthalate.

* * * * *